United States Patent [19]

Haskell

[11] Patent Number: 4,734,273

[45] Date of Patent: Mar. 29, 1988

[54] PROCESS FOR THE SELECTIVE REMOVAL OF TRACE AMOUNTS OF OXYGEN FROM GASES

[75] Inventor: Weston W. Haskell, Houston, Tex.

[73] Assignee: Shell Oil Company, Houston, Tex.

[21] Appl. No.: 946,734

[22] Filed: Dec. 29, 1986

[51] Int. Cl.$^4$ .............................................. C01B 13/00
[52] U.S. Cl. ........................................ 423/219; 55/68; 55/75; 55/76; 423/579; 502/416; 502/417; 585/809; 585/820
[58] Field of Search ................... 423/219, 579; 55/68, 55/75; 502/416, 417; 585/820, 823

[56] References Cited

U.S. PATENT DOCUMENTS

| | | | |
|---|---|---|---|
| 2,019,632 | 11/1935 | Ray ..................................... | 423/219 |
| 2,849,515 | 8/1958 | Leatherman et al. .................. | 55/76 |
| 2,962,343 | 11/1960 | Goedkoop ........................... | 423/219 |
| 3,962,129 | 6/1976 | Munzner et al. ..................... | 423/579 |
| 4,184,983 | 1/1980 | Putz et al. ........................ | 423/219 |
| 4,192,773 | 3/1980 | Yoshikawa et al. ................. | 423/219 |
| 4,366,085 | 12/1982 | Ikegami et al. ..................... | 423/219 |
| 4,516,984 | 5/1985 | Warner et al. ...................... | 423/219 |
| 4,528,281 | 7/1985 | Sutt, Jr. ............................. | 502/417 |
| 4,594,163 | 6/1986 | Sutt, Jr. ............................. | 208/310 R |
| 4,595,575 | 6/1986 | Oeste et al. ........................ | 423/219 |
| 4,617,182 | 10/1986 | Brown et al. ....................... | 423/579 |

Primary Examiner—W. J. Shine
Assistant Examiner—Anthony McFarlane

[57] ABSTRACT

A process is disclosed for selectively sorbing trace amounts of oxygen from low molecular weight olefins and inert gases by contacting with high surface area particulate coal-derived activated carbon having high ash and moisture content.

10 Claims, No Drawings

4,734,273

PROCESS FOR THE SELECTIVE REMOVAL OF TRACE AMOUNTS OF OXYGEN FROM GASES

BACKGROUND OF THE INVENTION

This invention relates to a process for treating gases contaminated with very minor amounts of oxygen. More particularly it is adapted to treating substantial flows of gaseous olefins and inert gases, and selectively reducing oxygen levels from a few parts per million by weight (ppmw) to levels less than about 0.3 ppmw. The treatment is accomplished by contacting the gas contaminated with oxygen as feed with a bed of certain coal derived activated carbon, under certain conditions, and separating from the bed a product gas having a reduced oxygen content.

Inert gas i.e. nearly oxygen-free gas is used in many industrial applications, such as e.g., for purging, blanketing, and for maintaining an inert atmosphere in material transport. The gas may be manufactured by stoichiometric combustion of hydrocarbon fuel in which case it contains carbon dioxide, water vapor, nitrogen and traces of oxygen, carbon monoxide, hydrogen and rare inert atmospheric gases such as argon; or cryogenically, in which case it primarily contains nitrogen, and traces of oxygen.

Particularly in the preparation of high molecular weight polymers, free oxygen must be excluded as much as possible from feed gases employed for many catalytic polymerization processes. Oxygen may be present as a contaminant in e.g. olefinic hydrocarbons as the result of the manufacturing process and/or during storage. For the polymerization of for example, ethylene and/or propylene, the presence of very minor amounts i.e. more than a few tenths of a part per million by weight, of oxygen may rapidly deactivate the catalyst, or otherwise adversely impact properties of the resulting polymer.

Various methods have been proposed for sorbing trace amounts of oxygen from these gaes. Japanese Pat. No. 061769 discloses the use of high molecular weight complexes of certain low molecular weight complexes of transition metal of groups VIA, VIII, IB and IIB of the fourth period of the periodic table, which are ligand substituted with water soluble high molecular weight ligands containing: (a) radicals having coordinating ability to the base metal, such as e.g., an amine radical, and (b) longchain alkyl radicals, such as e.g. dodecyl-, situated in the vicinity of radicals (a).

German Pat. No. 2,553,567 discloses that trace amounts of oxygen and other impurities may be sorbed from olefins and inert gases using sorbents prepared by impregnating a carrier material having a specific surface area of at least 1200 m$^2$/g and a specific pore volume of at least 0.5 cm$^3$/g with an aqueous solution of a manganese compound, activating at 60° to 600° C. under a pressure between 10 mm. of mercury and 5 atmospheres in an oxygen containing gas for for 5-300 minutes and treating the activated material with a reducing gas under a pressure between 10 mm of mercury and 5 atmospheres at 250°-600° C. for 1 to 60 minutes. Suitable carriers are silica gel, titanium dioxide, thorium oxide, zirconium oxide, magnesium oxide, magnesium hydroxide, magnesium carbonate, magnesium alcoholates, zeolites, or silica gel with a magnesium oxide surface layer.

Russian Pat. No. 706,387 discloses the use of an oxygen sorbent that contains 0.5-3% W $Cr_2O_3$ on silica gel.

Activated carbon is a well known gas and vapor sorbent. It is used to remove corrosive gases and vapors from intake air to protect equipment in telephone exchanges, and is also used to lengthen the storage life of apples in warehouses by removing ethylene from the atmosphere. Further it is known that wet activated carbon depletes oxygen from air; that workers entering a vessel containing carbon must take precautions since dangerously low levels of oxygen may be encountered. It has now been found that certain activated carbon may be used to selectively reduce even trace amounts of oxygen present in inert gases, and in polymerizable aliphatic olefin gases such as ethylene and propylene.

It is known from Johannes, C. Advances in Cryogenic Engineering, Vol. 17, pp 307-12 that activated carbon derived from cocoanut charcoal can reduce oxygen in Helium at 70° K. to levels of about 1.3 ppm. However, the use of such low temperatures is not practical for many industrial applications.

SUMMARY OF THE INVENTION

This invention provides a process for treating gases contaminated with up to about 10 parts per million of oxygen to reduce the level of contamination comprising:
(a) contacting at a temperature from about 10° to about 40° C. a gas containing up to about 10 parts per million by weight of oxygen with a bed of coal-derived activated carbon having a suface area from about 800 to about 2,000 square meters per gram, an ash content above 2.5 percent by weight, and a moisture content in the range from about 10 to about 30 percent by weight for a period of time sufficient to reduce the level of contamination, and
(b) separating from the carbon bed a gaseous product having reduced oxygen content.

DESCRIPTION OF PREFERRED EMBODIMENTS

The gases to be treated according to the oxygen removal process of the invention will genreally be synthetic gases manufactured to be oxygen-free such as, for example, inert gases produced by combustion of hydrocarbons or by cryogenic means, and gaseous olefins, particularly ethylene and propylene, as may be produced by thermal or catalytic cracking of petroleum hydrocarbons. Suitably the olefinic hydrocarbons are $C_2$ to $C_4$ aliphatic olefins having an atmospheric boiling point in the range below about 1° C., and will include ethylene, propylene, butene-1, butene-2, and 2-methylpropene-1. Conventionally such gases after their manufacture, shipping and storage, e.g. in underground caverns and the like, often contain minor amounts, e.g. 0.5-10 ppm of oxygen. For many applications, particularly when these gases are employed in catalytic processes, selective removal of the oxygen to levels below about 0.3 ppm is necessary or desirable.

The contacting of the gases contaminated with oxygen, with the sorbent according to the invention may take place by any known gas-solids contacting procedure e.g. by contacting of the gas with a moving or fluidized bed of sorbent particles, however, preferably and most conventionally, the oxygen is removed by passing the gas through a static bed of the granular sorbent at weight hourly space velocities from about 0.1 to about 10.0, preferably from about 04. to about 3.0, and most preferably from about 0.5 to about 2.5. The contact bed may be in any configuration adapted for the desired flow rate and the oxygen content of the gas. The sorbent is used in typical fashion. It is preferably used in a packed bed or column. The use of dual columns allow one to be regenerated for sorbing additional oxygen while the other is sorbing.

The activated carbon sorbents of this invention are porous, amorphous particulate solids having a surface area in the range from about 800 to about 2,000 square meters per gram, and preferably from about 1,000 to about 1,800 square meters per gram, as determined from the nitrogen adsorption isotherm by the Brunauer, Emmett and Teller Method (BET Method); and a moisture content from about 10 to about 30 percent by weight of water, determined by drying the carbon in an open vessel of three hours at 110° C. Typically activated carbon is manufactured and shipped with very low moisture content of about 2 percent by weight. This has been found unsuitable to selectively sorb oxygen from the inert gases according to the invention, which oxygen has extremely low partial pressure at the low concentration on the order of about 10 ppm.

Although some improvement in the oxygen sorption capabilities of the carbon may be found by increasing the moisture content by immersing the carbon in water and then draining the excess liquid from the carbon, by far the best results have been obtained when the moisture is added to the granular carbon by sorption from moist inert gas. Such gas preferably contains sufficient moisture to have a relative humidity of at least about 50% i.e. from about 50 to about 100% of the water saturation level in said gas at the temperature of contacting with the carbon. Although the temperature for such moisturizing, i.e. pretreatment of the carbon to obtain the desired moisture content is not critical, preferably the temperature is in the range from about 10° to about 40° C.

The activated carbon will preferably be derived from coal and will have an ash content of at least about 2.5 percent by weight; preferably in the range from about 6.5 to about 15 percent by weight ash. Ash is a measure of the inorganic matter present and is determined by comparing the weight of carbon remaining after heating a sample of the carbon from which moisture has previously been removed (3 h at 110° C.) in an oxidizing atmosphere at a tmeperature of 600° C. to constant weight of the remaining ash, with the weight of the original dried carbon. Activated carbon derived from cocoanut charcoal and having lower ash content has been found unsuitable as having little or no activity for removing oxygen in the process of the invention. Elemental analysis of the ash from activated carbon suitably used in the process according to the invention has found primarily silicon, calcium, aluminum, magnesium, iron and sodium.

For regeneration, heat alone is not suitable. The regeneration requires using a reducing gas to sweep through the bed at temperatures of e.g. 110° to 150° C. followed by contacting with a moisture-containing reducing gas at temperature of 10°–40° C. Hydrogen, carbon monoxide and mixtures thereof, are suitably used as the regeneration sweep gas.

In many instances the feed gas contaminated with oxygen will also contain moisture resulting from manufacture, storage or contact with aqueous solutions for removal of other impurities, e.g. contact with alkaline solutions to remove sulfur-containing impurities. In a preferred embodiment according to the invention, such moisture containing feed gas first contacts the carbon sorbent bed, and after separation contacts a bed of a granular drying agent such as e.g. a molecular sieve to remove the moisture only after the oxygen has been sorbed. In this manner the carbon bed will better retain the desired moisture content, then if the feed gas was first dried, before contacting the carbon bed. A particularly preferred embodiment uses dual columns, each containing both the activated carbon according to the invention, and a conventional molecular sieve granular drying agent having an average pore size less than about 5 Å, arranged such that the feed gas first contacts the carbon bed in the column used to selectively remove the oxygen containment. The contacting is disrupted to the columns alternately to allow for regeneration of the activated carbon bed and the molecular sieve drying bed simultaneously, and at least a portion of the desorbed moisture from the drying bed is recycled through the carbon bed, so that the moisture content of the carbon bed is in the range from about 10 to about 30 percent by weight on carbon upon resumption of contacting of said carbon bed with the feed gas.

It has been found that during regeneration the oxygen is not simply stripped from the carbon in molecular form, and at the low temperature regeneration carbon monoxide is not found in the regeneration effluent gas.

The process of this invention is illustrated by the following illustrative embodiments which are provided for illustration and comparative purposes and are not to be construed as limiting the invention.

ILLUSTRATIVE EMBODIMENT I

A 200 gram portion of a commercial granulated activated carbon having a surface area of about 1100 m$^2$/g, a pore volume of about 0.7 cc/g, an ash content of about 12.5% w, and an as received moisture content of about 2% w is loaded into a mild steel tube or column having a diameter about 4 cm and length of about 18 cm. and is retained in said column by a quantity of quartz wool at both the inlet and outlet ends of the column. The column is installed to receive a slip stream of an inert gas from a gas distribution system whereby cryogenic nitrogen is conveyed to a number of applications at ambient temperature, i.e. 20°–25° C. The feed gas is bubbled through water to assure that its moisture content is at least above 50% relative humidity. Oxygen content of the inert gas feed to and outlet from the column is continuously analyzed electrochemically by means of a Delta F oxygen analyzer. The oxygen content of the feed gas varies over time in the range from about 0.5 to about 8 ppm and the activated carbon bed is found to have little influence until sufficient moisture has been sorbed by the bed to raise the water content above about 10% w. The inert gas is fed to the column at a rate of about 60 l/h (weight hourly space velocity of about 1). The sorption rate of the activated carbon is sufficient to maintain the oxygen content of the column outlet gas below about 0.03 ppm. On one occasion owing to a breach in the distribution system the oxygen content of the gas feed to the column is increased to an undetermined value well above 10 ppm, and remains there for several hours, after which it returns to normal levels. The oxygen content of the column effluent gas exceeds 1 ppm during this excursion (the upper limit of the unslurried scale reading), but when the feed gas returns to oxygen content below about 10 ppm the activated carbon bed is again efficient to sorb and reduce the oxygen content of the column effluent gas below about 0.03 ppm. Eventually, after about three weeks of operation, the sorption capacity of the bed is reached, as indicated by an increase in the oxygen content of the column outlet gas, which increase is commensurate with an increase in the flow rate of the feed gas. The carbon bed is regenerated by elevating the temperature to about 140° C. for several hours, followed by cooling and flowing through the bed a stream of hydrogen as gas which has been moistened by bubbling through water at ambient temperature (@20° C.). The bed is found to have been satisfactorily regenerated. During the regeneration step the effluent gases from the carbon bed are monitored for oxygen. None is detected. Moisture in those same effluent gases is condensed in a cold trap and amounts to about 50 ml indicating that the final moisture content of the carbon bed is in the order of about 25% w.

ILLUSTRATIVE EMBODIMENT II

For comparison purposes the procedure of Illustrative Embodiment I is repeated except that a commercially available activated carbon derived from cocoanut charcoal is used. This carbon which typically has a surface area of about 1100 m²/g, and an ash content of less than 2% w, when dry is found to have no effect in reducing the oxygen content of the feed gas and when the carbon contains at least about 10% w moisture is rapidly exhausted (less than one day compared to about three weeks for the carbon of Example I).

ILLUSTRATIVE EMBODIMENT III

The procedure of Illustrative Embodiment I is repeated except that the feed gas is bottled with ethylene containing about 2 ppm oxygen. After the moisture content of the carbon increases above about 10% by weight, the oxygen content of the product gas from the column is reduced to and remains at about 0.03 ppm for three days until the test is terminated owing to exhausting of the ethylene from the bottle supply.

What is claimed is:

1. A process for treating gases selected from the group of $C_2$ to $C_4$ aliphatic olefins contaminated with up to about 10 parts per million of oxygen to reduce the level of contamination comprising:
    (a) contacting at a temperature from about 10° to about 40° C. and a weight hourly space velocity in this range from about 0.5 to about 3 a gas containing up to about 10 parts per million of oxygen with a bed consisting essentially of coal-derived activated carbon having a surface area from about 800 to about 2,000 square meters per gram, an ash content of at least about 2.5 percent by weight, and a moisture content in the range from about 10 to about 30 percent by weight for a period of time sufficient to reduce the level of contamination, and
    (b) separating from the carbon bed a gaseous product having reduced oxygen content.

2. A process as in claim 1 wherein said activated carbon has an ash content in the range from about 6.5 to about 15 percent by weight.

3. A process as in claim 1 wherein said gas contains moisture from about 50 to about 100 percent of the water saturation level in said gas at the temperature of contacting.

4. A process as in claim 1 wherein said gas is selected from ethylene and propylene.

5. A process as in claim 1 wherein said gas is ethylene containing up to about 5 parts per million by weight of oxygen and the separated gas contains less than about 0.2 parts per million by weight oxygen.

6. A process as in claim 1 wherein said weight hourly space velocity is in the range from about 0.75 to about 2.5.

7. A process as in claim 1 comprising the further step of contacting the separated gas with a molecular sieve drying bed to reduce the moisture content of the separated gas.

8. A process as in claim 7 wherein said contacting is disrupted for simultaneous regeneration of the activated carbon bed and molecular sieve drying bed by heat and/or pressure change, and during said regeneration at least a portion of the desorbed moisture from said drying bed is passed through said carbon bed so that the moisture content of said carbon bed is from about 10 to about 30 percent by weight on carbon upon resumption of contacting of said carbon bed with the contaminated gas.

9. A process for treating ethylene gas contaminated with up to about 10 parts per million by weight of oxygen to reduce the level of contamination which comprises:
    (a) contacting at a temperature from about 10° to about 40° C. a gas containing up to about 10 parts per million by weight of oxygen with a bed consisting essentially of coal-derived activated carbon having a surface area in the range from about 1000 to about 1800 square meters per gram, an ash content in the range from about 6.5 to about 15 percent by weight, and a moisture content in the range from about 13 to about 28 percent by weight, at a weight hourly space velocity in the range from about 0.5 to about 3.0 in order to reduce the level of contamination to 0.2 parts per million by weight or less, and
    (b) separating said ethylene from said activated carbon.

10. A process for treating ethylene gas contaminated with up to about 10 parts per million by weight of oxygen to reduce the level of contamination which comprises:
    (a) contacting at a temperature from about 10° to about 40° C. and a weight hourly space velocity from about 0.5 to about 3, a gas containing up to about 10 parts per million by weight of oxygen with a bed consisting essentially of coal-derived activated carbon having a surface area in the range from about 1000 to about 1800 square meters per gram, an ash content in the range from about 6.5 to about 15 percent by weight, and a moisture content in the range from about 13 to about 28 percent by weight, at a weight hourly space velocity in the range from about 0.5 to about 3.0 in order to reduce the level of contamination to 0.2 parts per million by weight or less;
    (b) separating said ethylene from said activated carbon;
    (c) contacting the separated ethylene with a molecular sieve drying bed to reduce the moisture content of the separated gas, and
    (d) intermittently disrupting said contact of steps (a) and (c) for simultaneous regeneration of the activated carbon bed and molecular sieve drying bed by heat and/or pressure change, and
    (e) passing at least a portion of the desorbed moisture from said drying bed during regeneration through said carbon bed so that the moisture content of said carbon bed is from about 10 to about 30 percent by weight on carbon upon resumption of contacting of said carbon bed with the contaminated gas.

* * * * *